United States Patent [19]

Steinmetz

[11] Patent Number: 4,904,817

[45] Date of Patent: Feb. 27, 1990

[54] PROCESS FOR THE PREPARATION OF AROMATIC CARBOXYLIC ACID ESTERS

[75] Inventor: Guy R. Steinmetz, Kingsport, Tenn.

[73] Assignee: Eastman Kodak Company, Rochester, N.J.

[21] Appl. No.: 312,983

[22] Filed: Feb. 21, 1989

[51] Int. Cl.[4] .................. C07C 67/36; C07C 51/10; C07C 17/00

[52] U.S. Cl. ........................ 560/80; 502/66; 502/185; 502/259; 502/261; 502/262; 502/326; 560/97; 560/100; 560/103; 562/406; 570/181

[58] Field of Search .................. 560/100, 103, 97, 80, 560/76; 562/406; 570/181; 502/66, 185, 259, 261, 262, 326

[56] References Cited

U.S. PATENT DOCUMENTS

| | | | |
|---|---|---|---|
| 2,565,462 | 8/1951 | Prichard et al. | 560/97 |
| 3,988,358 | 10/1976 | Heck | 560/97 X |
| 4,827,018 | 5/1989 | Rule et al. | 560/80 |
| 4,847,406 | 7/1989 | Steinmetz et al. | 560/80 |

FOREIGN PATENT DOCUMENTS

WO87/03629 6/1987 PCT Int'l Appl. .
WO87/03680 6/1987 PCT Int'l Appl. .

*Primary Examiner*—Werren B. Lone
*Assistant Examiner*—Vera C. Clarke
*Attorney, Agent, or Firm*—J. Frederick Thomsen; William P. Heath, Jr.

[57] ABSTRACT

Disclosed is an improved process for the manufacture of aromatic carboxylic acid esters by the carbonylation of aromatic iodides wherein the amount of the corresponding unesterified carboxylic acid in the product obtained from the process is minimized. The process comprises carbonylating an aromatic iodide in the presence of carbon monoxide, a Group VIII metal catalyst, an inorganic adsorbent and an alkanol to co-produce an aromatic carboxylic acid ester and an alkyl iodide.

10 Claims, No Drawings

PROCESS FOR THE PREPARATION OF AROMATIC CARBOXYLIC ACID ESTERS

This invention concerns a novel process for the manufacture of aromatic carboxylic acid esters by the carbonylation of aromatic iodides in the presence of an alkanol. More specifically, this invention concerns an improved process for the co-production of aromatic carboxylic acid esters and alkyl iodides by the carbonylation of aromatic iodides in the presence of a Group VIII metal catalyst, an inorganic absorbent and an alkanol.

The synthesis of aromatic carboxylic acids and esters by the carbonylation of aromatic iodides in the presence of a palladium or nickel catalyst and an alkanol is described in published PCT Patent Applications WO 0 87/036,279 and WO 87/036,280 published June 4, 1987. The presence of an alkanol in the processes is advantageous in that the iodine values originating from the aromatic iodide reactants may be recovered as alkyl iodides. However, the use of an alkanol results in the formation of water during the carbonylation process. The water thus formed causes the carbonylation product to contain a substantial amount of carboxylic acid, even when using a significant excess of the alkanol. The presence of free (unesterified) carboxylic acids can present purification problems when pure or essentially pure ester is desired. For example, in the manufacture of polyesters or other esters from the carbonylation product obtained as described above, it may be advantageous to use the ester or diester of the aromatic carboxylic acid or dicarboxylic acid.

U.S. Pat. No. 3,988,358 discloses the palladiumcatalyzed carbonylation of aromatic halides in the presence of alcohol and a tertiary amine to produce aromatic carboxylic acid esters. Nakayama and Mizoroki disclose in Bull. Chem. Soc. Japan 42 (1969) 1124 the nickel-catalyzed carbonylation of aromatic halides in the presence of an alkanol and potassium acetate to produce aromatic carboxylic acid esters. In these processes, the halide of the aromatic halide reactant is converted to an ammonium salt compound or an alkali salt from which the halogen values cannot be recovered in an economically-feasible manner.

U.S. Pat. No. 2,565,462 discloses the carbonylation of aromatic halides in the presence of alkanols, ethers and phenols and a carbonyl of iron, nickel or cobalt. The process described in this patent employs only noncatalytic amount of iron, nickel and cobalt which are used as promoters under reaction conditions much more severe than are required by my process.

The process of this invention provides for the coproduction of aromatic carboxylic acid esters, containing the corresponding unesterfied aromatic carboxylic acid, and alkyl iodides by the carbonylation of aromatic iodides whereby the unesterfied acid content of the product is decreased significantly below that present in the product obtained as described in the published PCT applications cited hereinabove. Carboxylic acid ester products with low levels of carboxylic acid groups permit simpler and less expensive production and purification schemes and eliminate the need for an esterification step. My process also provides for the recovery of iodine values as alkyl iodides. In accordance with my invention, an aromatic iodide is carbonylated, i.e., contacted with gaseous carbon monoxide, in the presence of a Group VIII metal catalyst selected from palladium, nickel, ruthenium, rhodium or mixtures thereof, an alkanol and an inorganic absorbent.

The aromtaic iodides, alkanols, Group VIII metal catalysts and the amounts thereof and the process conditions of pressure and temperature which may be utilized in my novel process are described generally in the published PCT applications cited hereinabove and also in Published PCT Applications WO 88/05036 and WO 88/05037 published July 14, 1988. The aromatic iodide reactant which may be used in our process may be mono- or poly-iodo, e.g. di- tri- and tetra-iodo aromatic compounds. The aromatic nucleus or moiety can contain from 5 to 18 carbon atoms and may be carbocyclic aromatic such as benzene, biphenyl, terphenyl, naphthalene, anthracene, etc. In addition to one or more iodine atoms, the aromatic moiety may be substituted by various substituents inert or relatively insert under the conditions employed in our process. Examples of such substituents include alkyl of up to about 12 carbon atoms such as methyl, ethyl, isobutyl, hexyl, 2-ethylhexyl, nonyl, decyl, dodecyl, etc.; cycloalkyl of about 5 to 12 carbon atoms such as cyclopentyl, cyclohexyl, 4-butylcyclohexyl, etc.; hydroxy; alkoxy of up to about 12 carbon atoms such as methoxy, ethoxy, propoxy, butoxy, octyloxy, etc.; halogen such as chloro; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of 2 to about 12 carbon atoms such as vinyl, allyl, etc.; formyl; alkanoyl of 2 to about 8 carbon atoms such as acetyl, propionyl, butyryl, hexanoyl, etc.; alkanoylamide of 2 to about 8 carbon atoms such as acetamido, butyramido, etc.; aroylamido such as benzamido; alkylsulfonyl of up to about b 8 carbon atoms such as methylsulfonyl, hexylsulfonyl, etc.; and alkylsulfonamido of up to about 8 carbon atoms such as methanesulfonamido, butanesulfonamido, etc.

The preferred reactants are benzene iodides and naphthalene iodides, i.e., mono- and poly-iodo benzenes and naphthalenes and mixtures thereof. Specific examples of the aromatic iodide reactants include iodobenzene, isomers of diiodobenzene, triiodobenzene, iodotoluene, iodophenol, iodoanisole, iodoacetophenone, diiodobiphenyl, chloroiodobenzene, bromoiodobenzene, diiodonaphthalene, triiodonaphthalene and the various isomers of such compounds. The process of this invention is particularly useful for the preparation of benzenedicarboxylic acid esters and naphthalenedicarboxylic acid esters with low acid content and thus the preferred reactants are diiodobenzene, especially 1,3- and 1,4-diiodobenzene and diiodonaphthalene, especially 2,6- and 2,7-diiodonaphthalene.

The aromatic iodide reactants are known compounds or mixtures of compounds and/or can be prepared according to published procedures. A number of such process are disclosed in T. Hudlicky et al, *The Chemistry of Halides, Pseudohalides and Azides*, Supplement D, Part 2, 1142–1158, J. Chem. Soc., (1952), 150,.European patent application Nos. 181,790 and 183,579, Japanese Patent No. 58/77830, Japanese patent application No. 57/77,631 and Bull. Chem. Soc. Japan, 47 (1974) 147.

Our process is carried out in the presence of an alkanol compound capable of forming an alkyl iodide under the carbonylation conditions. Examples of the alkanols which may be used include methanol, ethanol, propanol, butanol, pentanol, hexanol, 2-ethylhexanol, octanol, decanol and the like. The alkanols of up to about 4 carbon atoms are the preferred alkyl iodideforming compounds. Methanol is particularly preferred since it is the least expensive and produces methyl iodide which is the most volatile of the alkyl iodides.

Normally, at least one mole equivalent of alkanol should be use for each mole equivalent of aromatic iodide reactant. Typically, the alkanol, preferably methanol, is present in an amount which is about 50 to 300 mole percent greater than the moles of compounds constituting the aromatic iodide reactant.

The process provided by this invention may be carried out in the presence of an organic solvent depending on the conditions and apparatus employed. Examples of such solvents include aliphatic, alicyclic and aromatic hydrocarbons such as benzene, toluene, the xylenes, hexane, heptane, chlorobenzene, ethylene dichloride, methylchloroform, naphthalene, acetic acid, benzoic acid, methyl benzoate and the like. However, the use of such a co-solvent is not essential.

The Group VIII metal catalyst may be palladium, rhodium, nickel or ruthenium which may be used as the zero-valent metal or in the form of various salts or complexes which can be reduced to an active catalyst. Examples of the compounds which may be used in my process to provide the requisite Group VIII metal catalyst include palladium acetate, palladium chloride, rhodium trichloride, rhodium tribromide, rhodium triiodide, rhodium acetate, rhodium oxide, dicarbonyl rhodium acetylacetonate, rhodium carbonyl complexes including halide-substituted analogs, nickel acetate, nickel chloride, nickel iodide, ruthenium trichloride, ruthenium tribromide, ruthenium triiodide, ruthenium acetate, ruthenium acetylacetonate, ruthenium dioxide, ruthenium tetroxide, ruthenium carbonyl complexes such as ruthenium pentacarbonyl, dodecacarbonyltriruthenium and the halide-substituted analogs thereof. The catalysts also may be one of the aforesaid noble metals deposited on a suitable support or carrier such as carbon, alumina, silica-alumina, barium sulfate or zinc oxide.

The preferred Group VIII metal catalyst for the process of this invention is palladium.

The catalytically-effective amount of the catalyst can vary substantially depending on a number of factors such as the particular metal used, the reaction conditions, the conversion rate and yield desired, the mode of operation and the like. For example, with reference to the above-described metals as a group, the concentration of the catalytic metal in the reaction mixture may be within the range of about 0.0001 to 10.0 mole percent, preferably 0.001 to 0.500 mole percent, based on the moles of aromatic halide reactant. However, in certain modes of operation such as in a continuous process using a fixed-bed catalyst, the amounts of catalyst and reactant present is difficult, if not impossible, to determine.

Typically, the palladium catalyst is present in a concentration of 0.0001 to 1.0 mole percent, preferably 0.001 to 0.25 mole percent, based on the moles of aromatic iodide reactant. Therefore, the total reaction medium has a palladium concentration of about 0.1 to 1000 ppm with a preferred concentration of 1.0 to 250 ppm. When the catalyst is rhodium, it is normally present in a concentration of 0.001 to 10 mole percent, preferably 0.01 to 1.0 mole percent (same basis). The rhodium concentration in the total reaction medium therefore is in the range of 10 to 10,000 ppm, preferably 100 to 1000 ppm.

The catalytically-effective amount of nickel is in the range of 0.001 to 10.0 mole percent and preferably in the range of 0.1 to 2.5 mole percent (same basis). The total reaction medium thus will contain about 1.0 to 10,000 ppm, preferably 100 to 1000 ppm, nickel. Ruthenium may be used in a concentration of 0.01 to 10.0, preferably 0.1 to 1.0, mole percent. Therefore, the concentration of ruthenium in the total reaction medium is about 10 to 10,000 ppm and preferable about 200 to 1000 ppm.

The inorganic absorbent which is present in the process provided by this invention may be selected from silicas, aluminas, aluminophosphates, aluminosilicates (zeolites) such as molecular sieves, or mixtures thereof. Zeolites having a wide range of pore sizes such as large pore, e.g., X- and Y-zeolites, medium pore, e.g., ZSM-5 and small pore, e.g., A-zeolites, zeolites with varying ratios of silica to alumina may be used. These zeolites are further characterized by the presence of at least one alkali, alkaline earth, transition metal or lanthanide cation. Examples of such cations include sodium, potassium, rubidium, cesium, magnesium, calcium, palladium, lanthanum and cerium which are exchangeable according to known procedures. The zeolite lattice also can be modified by a large number of tri- and tetravalent atoms such as by replacing aluminum with boron, iron, chromium, antimony, arsenic and gallium and replacing silicon with germanium, titanium, zirconium and hafnium. Alternatively, the zeolite absorbent may be used in its acidic form wherein the cation sites of the zeolite are replaced by protons, for example, by treating the zeolite with an aqueous solution of an inorganic acid such as hydrochloric or nitric acid. The zeolite absorbents are described in detail in Chemical Engineering Progress, February, 1988, page 42 and Angew. Chem. Int. Ed. Engl. 27 (1988) 226. The 3A and 4A zeolites are the preferred absorbents due to their large absorption capacity for water at elevated temperatures and their small pore size which is highly selective for small molecules such as water.

The absorbent can be used in situ or external to the reaction mixture. The amount of absorbent is not critical provided a sufficient amount is present to decrease the amount of water present, i.e., in the reactants or the alkyl iodide-forming compound and/or formed as a result of the carbonylation and alkyl iodide-forming reactions, to the level desired or to maintain the water concentration at a predetermined level. The amount of absorbent used is dependent upon the mode of operation but typically is in the range of about 10 to 1000 weight percent based on the total weight of the reaction mixture or crude product mixture. After the absorbent is saturated, it can be removed or isolated from the process and regenerated, for example, by heating the saturated absorbent to desorb the water and other absorbates.

The process of my invention is conducted in the presence of carbon monoxide which may be essentially pure or it may contain other gases such as carbon dioxide, hydrogen, methane and other compounds produced by synthesis gas plants. Normally, the carbon monoxide is at least 90 preferably at least 95, percent pure.

The process is carried out at carboxylic acid ester-forming and alkyl iodide-forming conditions of pressure and temperature. The temperature and pressure are interdependent and can vary considerably. While pressures as high as 10,000 psig can be employed, the cost of utilities and equipment required for such a high pressure operation cannot normally be commercially justified. Accordingly, the pressure normally will be in the range of about 125 to 4000 psig with about 300 to 1500 psig being preferred. A particularly preferred pressure is about 1000 psig. The process normally is carried out at a temperature or about 125° to 225° C. although temperatures moderately higher or lower than those mentioned may be used if desired. The preferred temperature range is about 130° to 170° C. with a temperature of about 150° C. being especially preferred.

When a polyiodo aromatic compound is used in my carbonylation process, the products obtained include both aromatic polycarboxylic acid esters and partially carbonylated compounds such as iodoaromatic carboxylic acid esters. The relative amounts of partially or completely carbonylated products are dependent on the contact time of the reactants and catalyst under ester forming conditions. However, partially carbonylated compounds such as iodoaromatic carboxylic acid esters are useful as intermediates in the preparation of derivatives of aromatic esters such as compounds which may be obtained by nucleophilic displacement reactions wherein the iodo is replaced by various other nucleophiles according to known procedures.

Our process is particularly useful for the preparation of dialkyl esters of aromatic dicarboxylic acids such as 1,3- and 1,4-benzenedicarboxylic and 2,6- and 2,7-naphthalenedicarboxylic acid esters. Such diester compounds, such as dimethyl 2,6-naphthalenedicarboxylate, can be reacted with diols to produce high molecular weight polyesters, e.g., poly(ethylene terephthalate) and poly(ethylene naphthalenedicarboxylate), useful in the molding and extrusion of various articles.

The alkyl iodides which are a co-product of my novel process may be used in other chemical process such as in the preparation of carboxylic acids and anhydrides according to known carbonylation procedures. Alternatively, the alkyl iodides can be oxidatively decomposed at elevated temperatures to produce a gaseous mixture of iodine, carbon dioxide and water from which the iodine can be recovered. The iodine also may be recovered by thermal decomposition of the alkyl iodides to iodine and an alkane.

The process provided by this invention includes the formation of an alkyl iodide. Thus, the carbonylation reaction is carried out in the absence of any significant amounts of basic materials which preferentially combine with hydrogen iodide to form salts and thus interfere with or prevent the formation and recovery of an alkyl iodide. Examples of such iodide salt-forming bases which are essentially absent from the carbonylation reaction include amines, particularly tertiary amines, and hydroxides, alkoxides and weak acid salts such as carboxylates of the alkali and alkaline earth metals. Although certain of the inorganic absorbents described hereinabove contain alkali metal cations, such absorbents may be employed by positioning the absorbent, e.g., in the form of absorbent beds, external to the carbonylation reactor in a manner which permits the reactor off-gas to be circulated through the absorbent to selectively remove water from the process effluent and not affect to any significant degree the formation and recovery of an alkyl iodide. A number of the inorganic absorbents may be used within the carbonylation reactor, i.e., in contact with the liquid reaction mixture, without affecting to a significant degree the formation and recovery of an alkyl iodide when the process is operating at steady state. Satisfactory performance of such an internal absorbent depends upon a number of factors such as base strength, pore size and the economic necessity to recover all of the iodide as an alkyl iodide.

As described hereinabove, my novel process provides for the preparation of carboxylic acid esters which contain low levels of free carboxylic acid groups. The mole ratio of ester groups to acid groups in the crude product obtained from the process is dependent upon the mode of operation but typically is a least 25 and preferably at least 50.

The process of this invention can be carried out as a batch, semi-continuous or continuous operation. In the manufacture of dialkyl esters of aromatic dicarboxylic acids in the quantities required for the preparation of polyesters such as those mentioned above, the process will be conducted in a continuous manner. A typical continuous method of operating the process comprises feeding into a mixed pressure vessel a liquid stream of an alkanol such as methanol, another liquid stream composed of an aromatic iodide such as 2,6-diiodonaphthalene, with or without an organic solvent, and the Group VIII metal catalyst and a gaseous stream of carbon monoxide. The reaction mixture or its gaseous vapors can be passed through a series of absorbent beds to remove water co-produced in the reaction. These absorbent beds can be isolated independently so that one or more beds can be regenerated in a continuous process. The pressure vessel is equipped with means for maintaining the desired temperature and pressure. The liquid mixture from the reactor is passed to a flash column where the alkyl iodide and organic solvent may be flashed off. The flashed vapor stream is then condensed and the alkyl iodide and alkanol separated by decanting. The liquid underflow from the flash column is centrifuged and any carboxylic acid is separated from the solution containing the ester of the carboxylic acid. The desired carboxylic acid ester is then recovered by selective crystallization and the remaining mixture containing unreacted aromtaic iodide and catalyst is recycled.

The process of this invention is further illustrated by the following examples. In the procedures utilized in the examples the materials employed are loaded into a 330 mL autoclave constructed of Hastelloy B2 alloy and designed to operate in a rocking mode. The autoclave is pressurized with 500 psig carbon monoxide gas pressure at room temperature and then the gas is vented and the autoclave is sealed. The autoclave then is pressurized to 200 psig with carbon monoxide at ambient temperature and heated and rocked until reaction temperature is reached, at which time additional carbon monoxide is added to increase the autoclave internal pressure to the predetermined value. This point in the procedure represents the beginning of the reaction time. Reactor pressure is maintained by adding carbon monoxide t the same rate as it is consumed by the reactant. The carbon monoxide used is essentially pure. When the predetermined reaction time is completed, the autoclave is cooled by a stream of cold air to approximately 25° C. After the gas is vented from the autoclave, the crude product is analyzed by gas chromatographic methods. The percent conversion is the mole percent of iodo groups converted to carboxylic acid or ester groups. The ester:acid ratio is the mode ratio of total ester and acid groups formed.

Using the above procedure, 2,6-diiodonaphthalene is carbonylated in the presence of methanol, toluene and palladium acetate catalyst at 150° C. In Examples 1, 2 and 3, 4A molecular sieves adsorbent is included in the initial reaction mixture whereas sodium 13X molecular sieves adsorbent is used in Example 4. In Control Example 1 (C-1), no adsorbent was employed. The Table shows the amount (g) of 2,6-diiodonaphthalene, methanol, toluene and adsorbent, the reaction time (Time, minutes) and the pressure (psig) used in each of the examples. The Table gives the amount of catalyst used in mg [Pd]. The % conversion values and the ester:acid ratios given for each example have the meanings described above.

TABLE

|  | Examples | | | | |
| --- | --- | --- | --- | --- | --- |
|  | 1 | 2 | 3 | 4 | C-1 |
| Diiodonaph. | 40.04 | 40.15 | 40.00 | 40.00 | 40.00 |
| Methanol | 38.96 | 41.75 | 38.31 | 38.70 | 38.22 |
| Toluene | 85.94 | 81.01 | 82.56 | 72.12 | 85.46 |
| Adsorbent | 5.02 | 10.04 | 50.03 | 100.08 | — |
| Catalyst | 2.0 | 50.3 | 49.3 | 5.9 | 2.0 |
| Time | 120 | 180 | 210 | 180 | 250 |
| Pressure | 750 | 1000 | 1000 | 1000 | 750 |
| % Conv. | 88.31 | 100 | 100 | 100 | 100 |
| Ester:Acid | 28.1 | 34.6 | 68.6 | 128.9 | 8.9 |

The invention has been described in detail with particular reference to preferred embodiments thereof, but it will be understood that variations and modifications will be effect within the spirit and scope of the invention.

I claim:

1. Process for the co-production of an aromatic carboxylic acid ester, containing the corresponding unesterfied aromatic carboxylic acid, and an alkyl iodide which comprises carbonylating an aromatic iodide in the presence of carbon monoxide, a Group VIII metal catalyst selected from the group consisting of palladium, nickel, ruthenium, rhodium and mixtures thereof, an inorganic absorbent and an alkanol at carboxylic acid ester-forming and alkyl iodide-forming conditions of pressure and temperature, wherein the mole ratio of carboxylic acid ester groups to unesterified carboxylic acid groups in the crude product is at least 25.

2. Process according to claim 1 wherein the inorganic absorbent is selected from the group consisting of silicas, aluminas, aluminophosphates and aluminosilicates.

3. Process according to claim 1 for the co-production of an aromatic carboxylic acid ester, containing the corresponding unesterfied aromatic carboxylic acid and an alkyl iodide which comprises carbonylating an aromtaic iodide in the presence of carbon monoxide, a Group VIII metal catalyst selected from the group consisting of palladium, nickel, ruthenium, rhodium and mixtures thereof, a crystalline aluminosilicate zeolite absorbent and an alkanol having up to about 4 carbon atoms at a pressure of about 125 to 4000 psig and a temperature of about 125° to 225° C.

4. Process according to claim 1 for the co-production of an aromatic dicarboxylic acid diester, containing the corresponding unesterfied aromatic carboxylic acid or the monoester thereof, and an alkyl iodide which comprises carbonylating an aromatic diiodide in the presence of carbon monoxide, a Group VIII metal catalyst selected from the group consisting of palladium, nickel, ruthenium, rhodium and mixtures thereof, a crystalline aluminosilicate zeolite absorbent and an alkanol having up to about 4 carbon atoms at a pressure of about 125 to 4000 psig and a temperature of about 125° to 225° C.

5. Process according to claim 1 for the co-production of dialkyl 1,3- or 1,4-benzenedicarboxylate, containing the corresponding unesterified carboxylic acid or the mono-ester thereof, and an alkyl iodide which comprises carbonylating 1,3- or 1,4-diiodobenzene in the presence of carbon monoxide, a Group VIII metal catalyst selected from the group consisting of palladium, nickel, ruthenium, rhodium and mixtures thereof, a crystalline aluminosilicate zeolite absorbent and an alkanol having up to about 4 carbon atoms at a pressure of about 125 to 4000 psig and a temperature of about 125° to 225° C.

6. Process according to claim 5 wherein the Group VIII metal catalyst is palladium, the absorbent is a 3A or 4A crystalline aluminosilicate, the pressure is in the range of about 300 to 1500 psig, the temperature is in the range of about 130° to 170° C. and the ratio of carboxylic acid ester groups to unesterified carboxylic acid groups is at least 50.

7. Process for the co-production of dimethyl 1,3- or 1,4-benzenedicarboxylate, containing the corresponding unesterfied benzenedicarboxylic acid or the mono-ester thereof, and methyl iodide which comprises carbonylating 1,3- or 1,4-diiodobenzene in the presence of carbon monoxide, a palladium catalyst, a 3A or 4A crystalline aluminosilicate zeolite absorbent and methanol at a pressure of about 300 to 1500 psig and a temperature of about 130° to 170° C., wherein the mole ratio of carboxylic acid ester groups to unesterfied carboxylic acid groups is at least 25.

8. Process according to claim 1 for the co-production of a dialkyl 2,6- or 2,7-naphthalenedicarboxylate, containing the corresponding unesterified naphthalenedicarboxylic acid or monoester thereof, and an alkyl iodide which comprises carbonylating 2,6- or 2,7-diiodonaphthalene in the presence of carbon monoxide, a Group VIII metal catalyst selected from the group consisting of palladium, nickel, ruthenium, rhodium and mixtures thereof, a crystalline aluminosilicate zeolite absorbent and an alkanol having up to about 4 carbon atoms at a pressure of about 125 to 4000 psig and a temperature of about 125° to 225° C.

9. Process according to claim 8 wherein the Group VIII metal catalyst is palladium, the absorbent is a 3A or 4A crystalline aluminosilicate, the pressure is in the range of about 300 to 1500 psig, the temperature is in the range of about 130° to 170° C. and the mole ratio of carboxylic acid ester groups to unesterified carboxylic acid groups is at least 50.

10. Process for the co-production of dimethyl 2,6- or 2,7-naphthalenedicarboxylate, containing the corresponding unesterified naphthalenedicarboxylic acid or mono-ester thereof, and methyl iodide which comprises carbonylating 2,6- or 2,7-diiodobenzene in the presence of carbon monoxide, a palladium catalyst, a 3A or 4A crystalline aluminosilicate zeolite absorbent and methanol at a pressure of about 300 to 1500 psig and a temperature of about 130° to 170° C. wherein the mole ratio of carboxylic acid ester groups to unesterified carboxylic acid groups is at least 50.

* * * * *